(12) United States Patent
Goetz et al.

(10) Patent No.: US 7,837,727 B2
(45) Date of Patent: Nov. 23, 2010

(54) MINIMALLY INVASIVE HEART VALVE REPLACEMENT

(75) Inventors: Wolfgang Goetz, Regensburg (DE); Hou-Sen Lim, Singapore (SG)

(73) Assignee: Transcatheter Technologies GmbH, Regensburg (DE)

( * ) Notice: Subject to any disclaimer, the term of this patent is extended or adjusted under 35 U.S.C. 154(b) by 13 days.

(21) Appl. No.: 12/192,872

(22) Filed: Aug. 15, 2008

(65) Prior Publication Data

US 2009/0005863 A1   Jan. 1, 2009

Related U.S. Application Data

(63) Continuation of application No. PCT/IB2007/003850, filed on Feb. 15, 2007.

(60) Provisional application No. 60/774,821, filed on Feb. 16, 2006.

(51) Int. Cl.
*A61F 2/24* (2006.01)

(52) U.S. Cl. ............... 623/2.18; 623/1.24; 623/1.15

(58) Field of Classification Search .......... 623/2.1, 623/2.11, 2.14, 2.17, 2.18, 1.1, 1.15, 1.24, 623/1.14
See application file for complete search history.

(56) References Cited

U.S. PATENT DOCUMENTS

| 3,657,744 | A | 4/1972 | Ersek |
| 6,830,585 | B1 | 12/2004 | Artof et al. |
| 7,041,132 | B2 | 5/2006 | Quijano et al. |
| 2005/0075584 | A1 | 4/2005 | Cali |
| 2005/0075731 | A1 | 4/2005 | Artof et al. |
| 2005/0137689 | A1 | 6/2005 | Salahieh et al. |
| 2005/0137695 | A1 | 6/2005 | Salahieh et al. |
| 2005/0143809 | A1 | 6/2005 | Salahieh et al. |
| 2005/0240200 | A1 | 10/2005 | Bergheim |
| 2005/0267573 | A9 | 12/2005 | Macoviak et al. |

FOREIGN PATENT DOCUMENTS

| WO | WO 00/47139 | 8/2000 |
| WO | WO 2004/103223 | 12/2004 |

*Primary Examiner*—David H Willse
*Assistant Examiner*—Matthew Schall
(74) *Attorney, Agent, or Firm*—Fitch, Even, Tabin & Flannery

(57) ABSTRACT

A replacement valve for implantation centrally within the orifice of a malfunctioning native heart valve. The valve is designed for minimally invasive entry through an intercostal opening in the chest of a patient and an opening in the apex of the human heart. The replacement valve includes either a separate anchor (11, 87, 111) or a combined anchor (67) that folds around the malfunctioning native valve leaflets, sandwiching them in a manner so as to securely anchor the replacement valve in a precise, desired location.

14 Claims, 9 Drawing Sheets

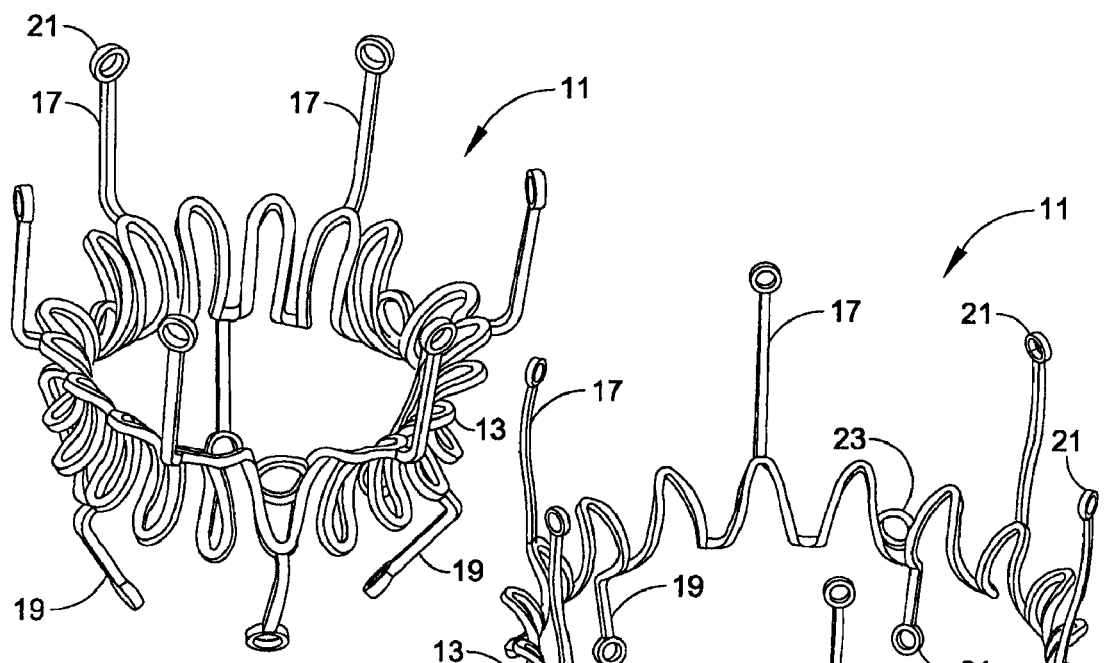
FIG. 1
FIG. 2
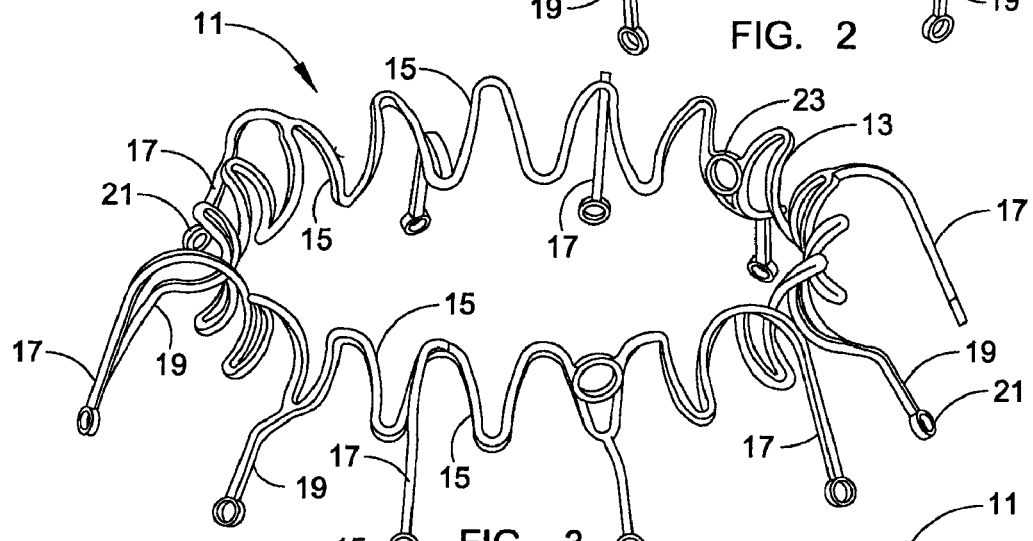
FIG. 3
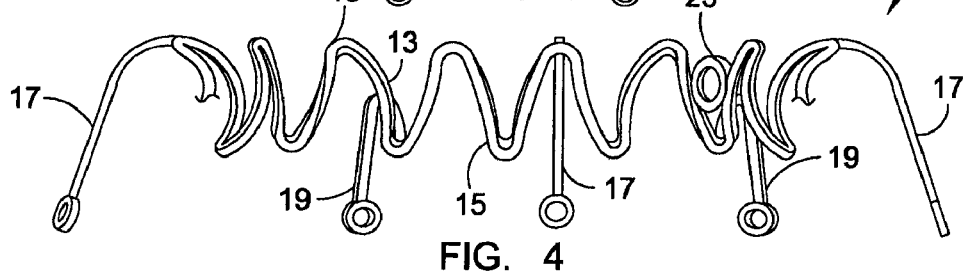
FIG. 4

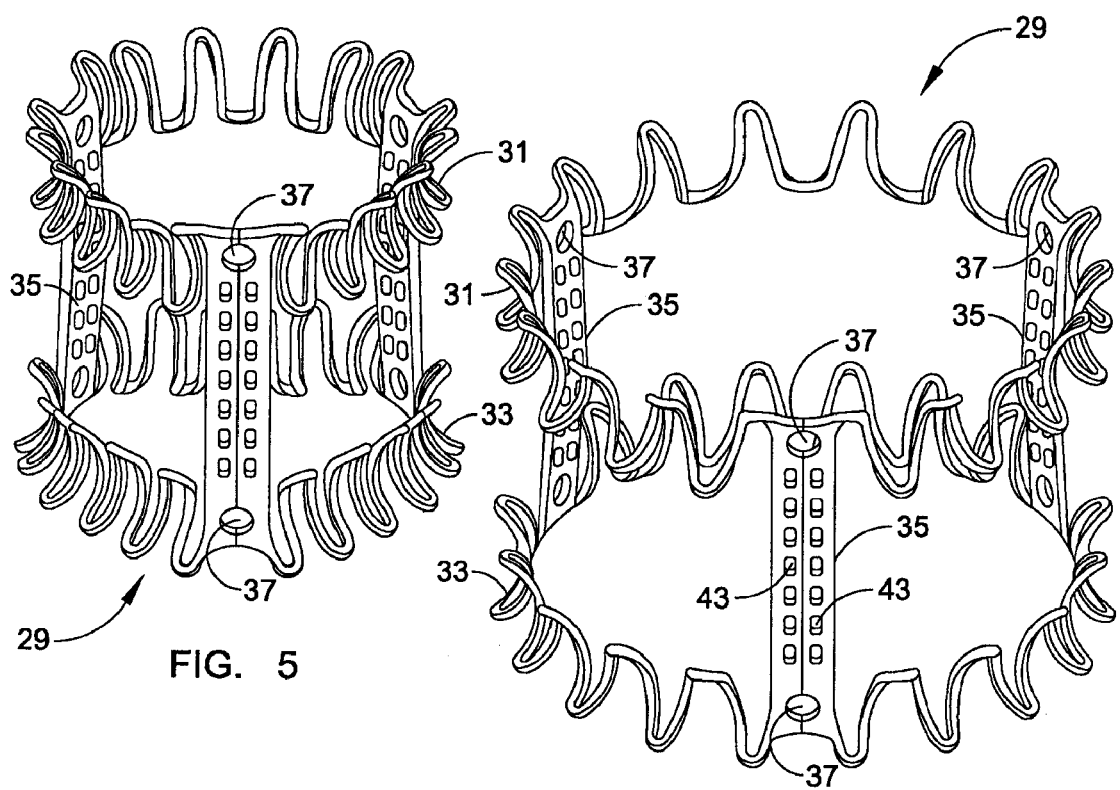
FIG. 5
FIG. 6
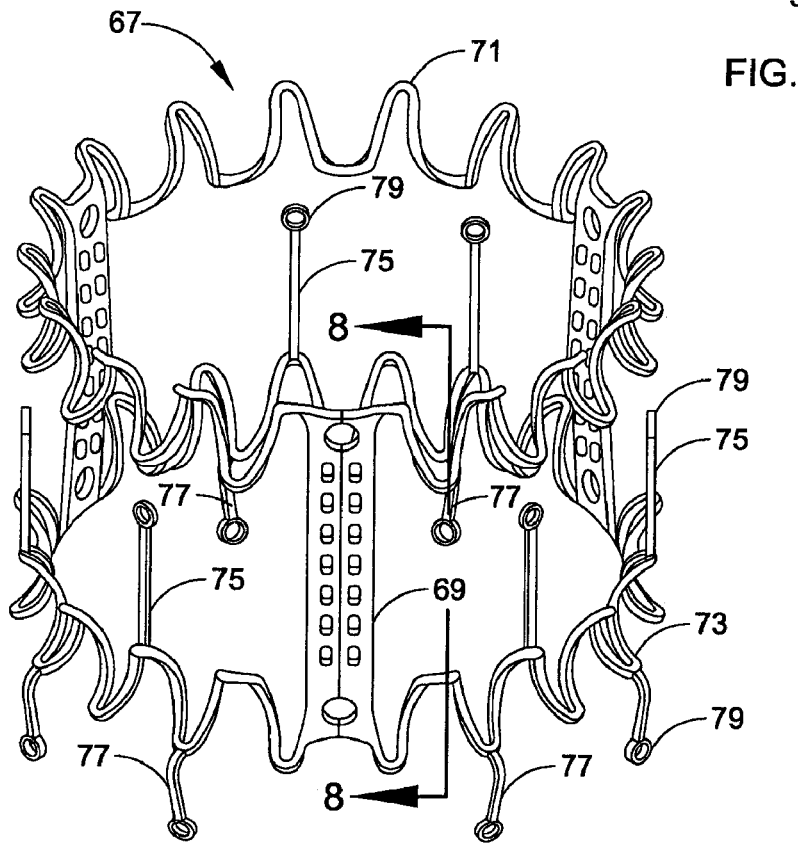
FIG. 7
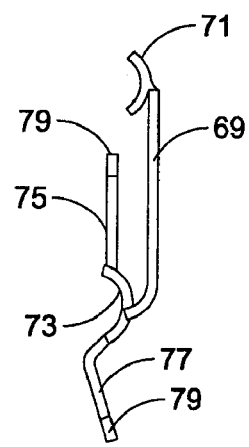
FIG. 8

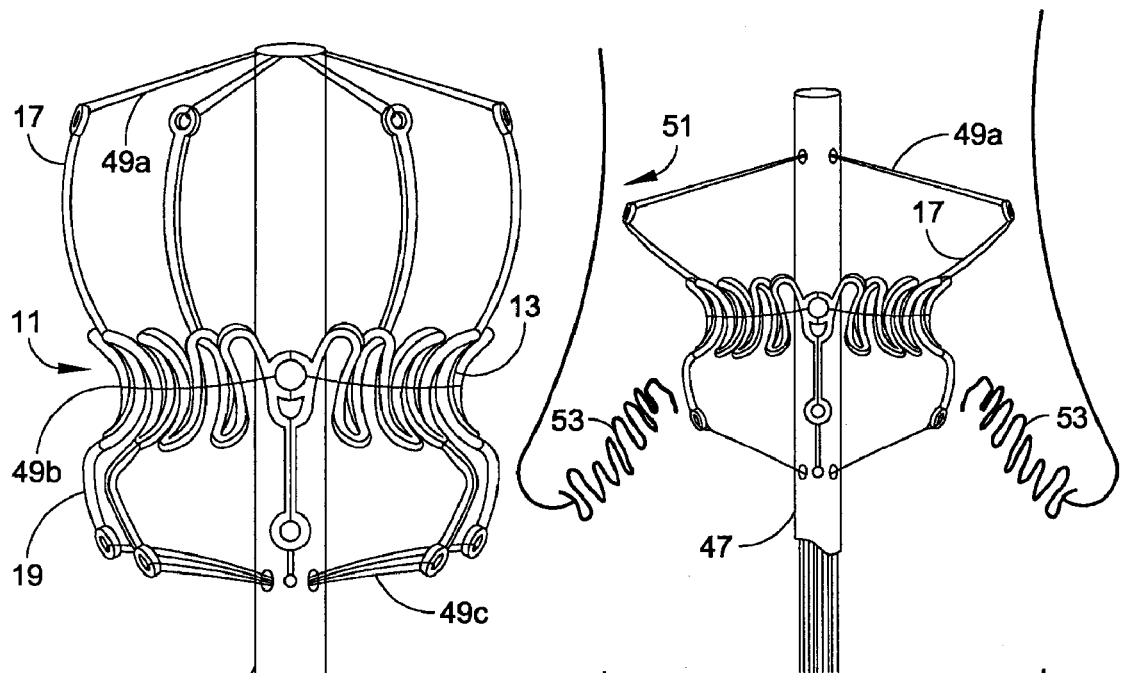
FIG. 13
FIG. 14
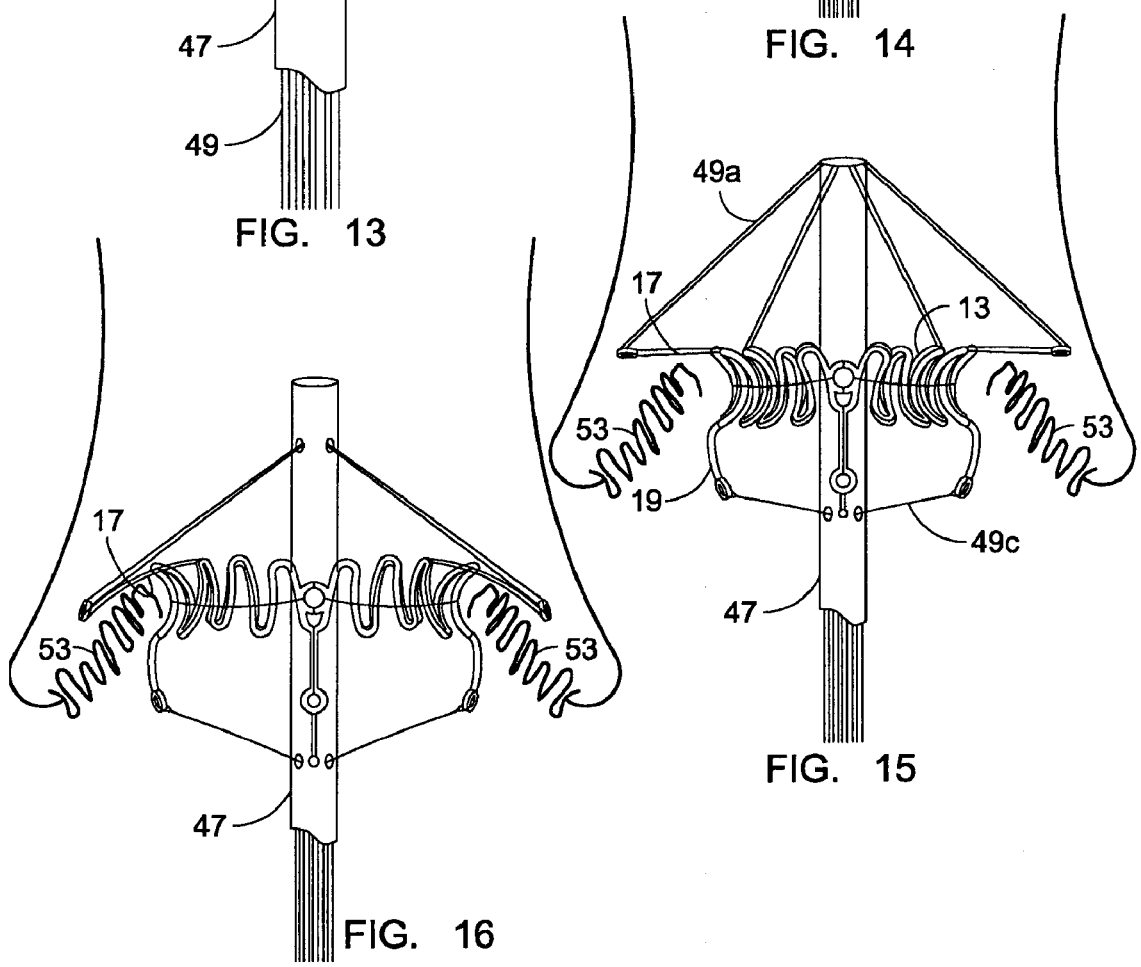
FIG. 16
FIG. 15

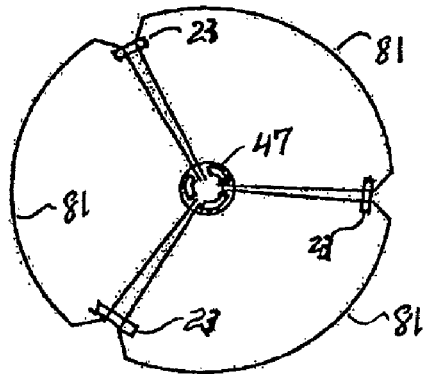
FIG. 25
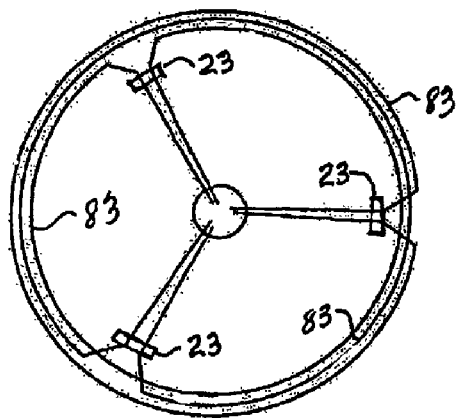
FIG. 26
FIG. 27
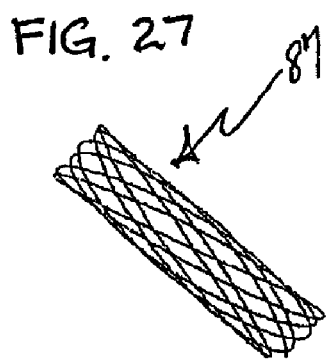
FIG. 28
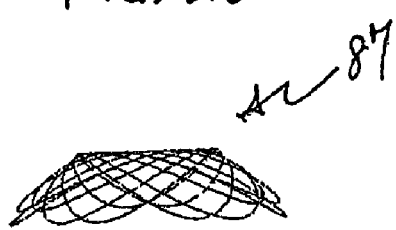

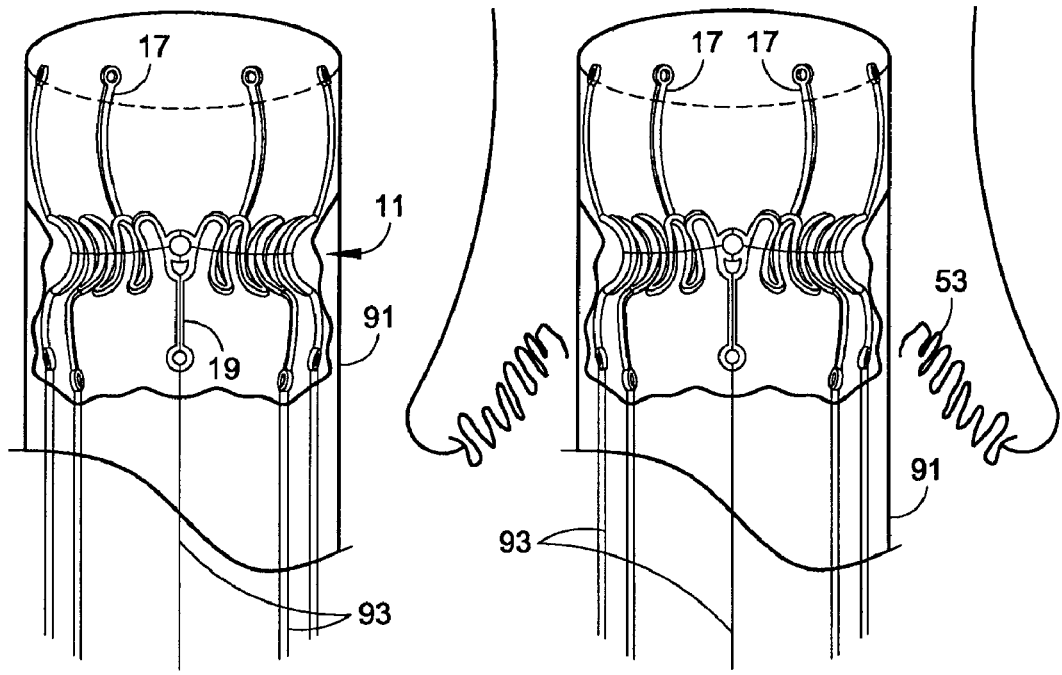
FIG. 29    FIG. 30
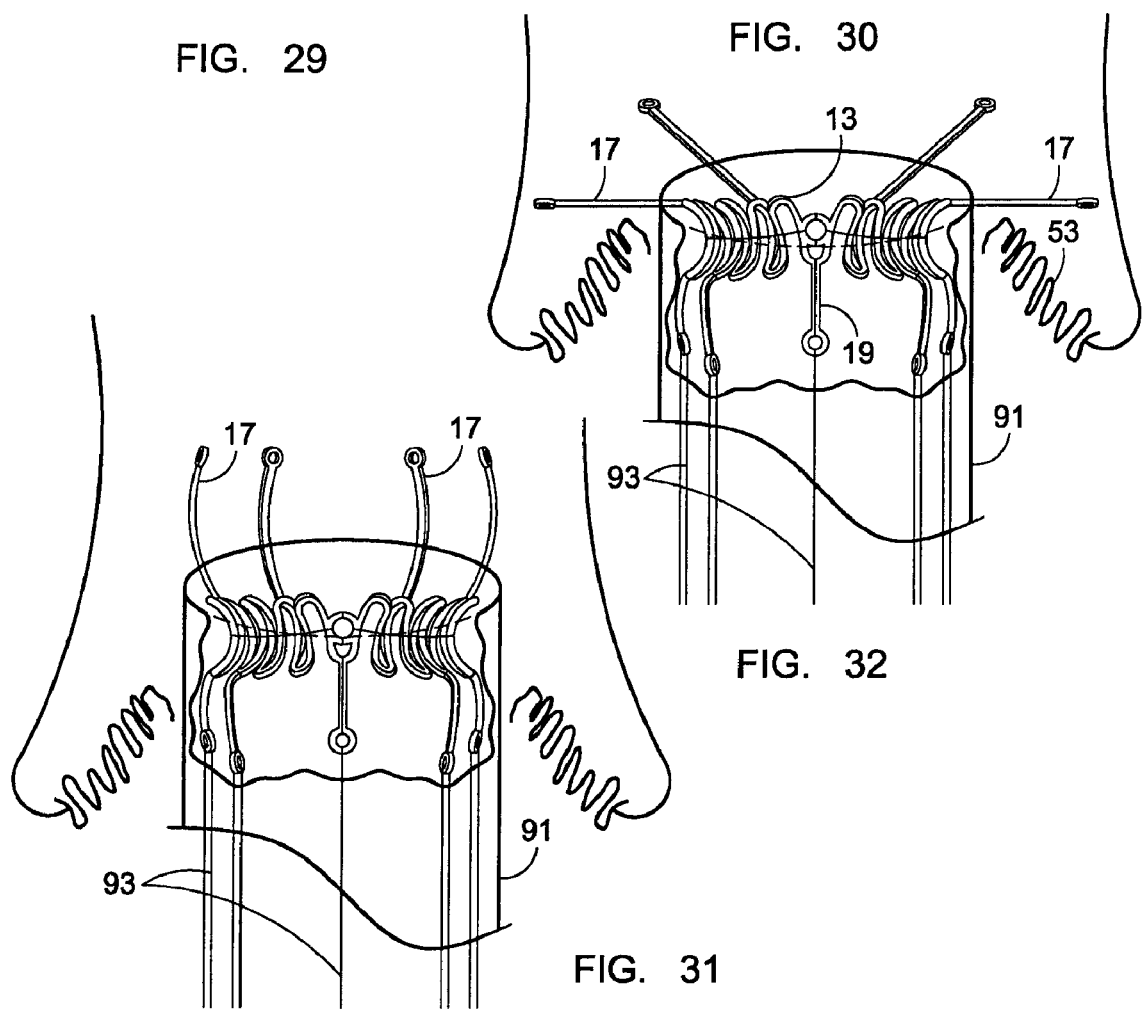
FIG. 32
FIG. 31

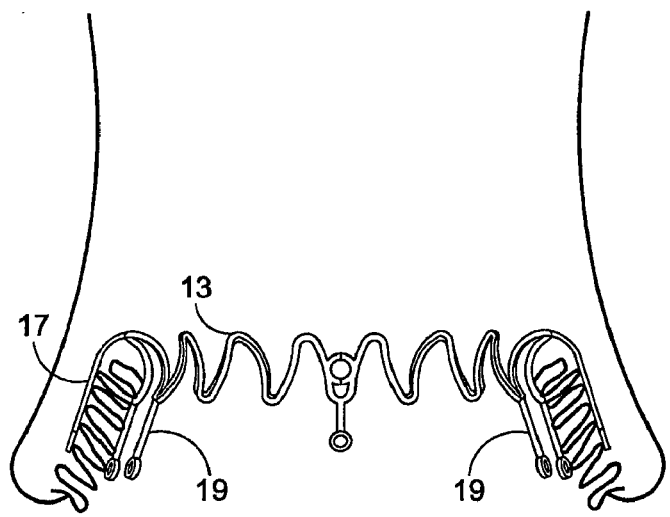
FIG. 34
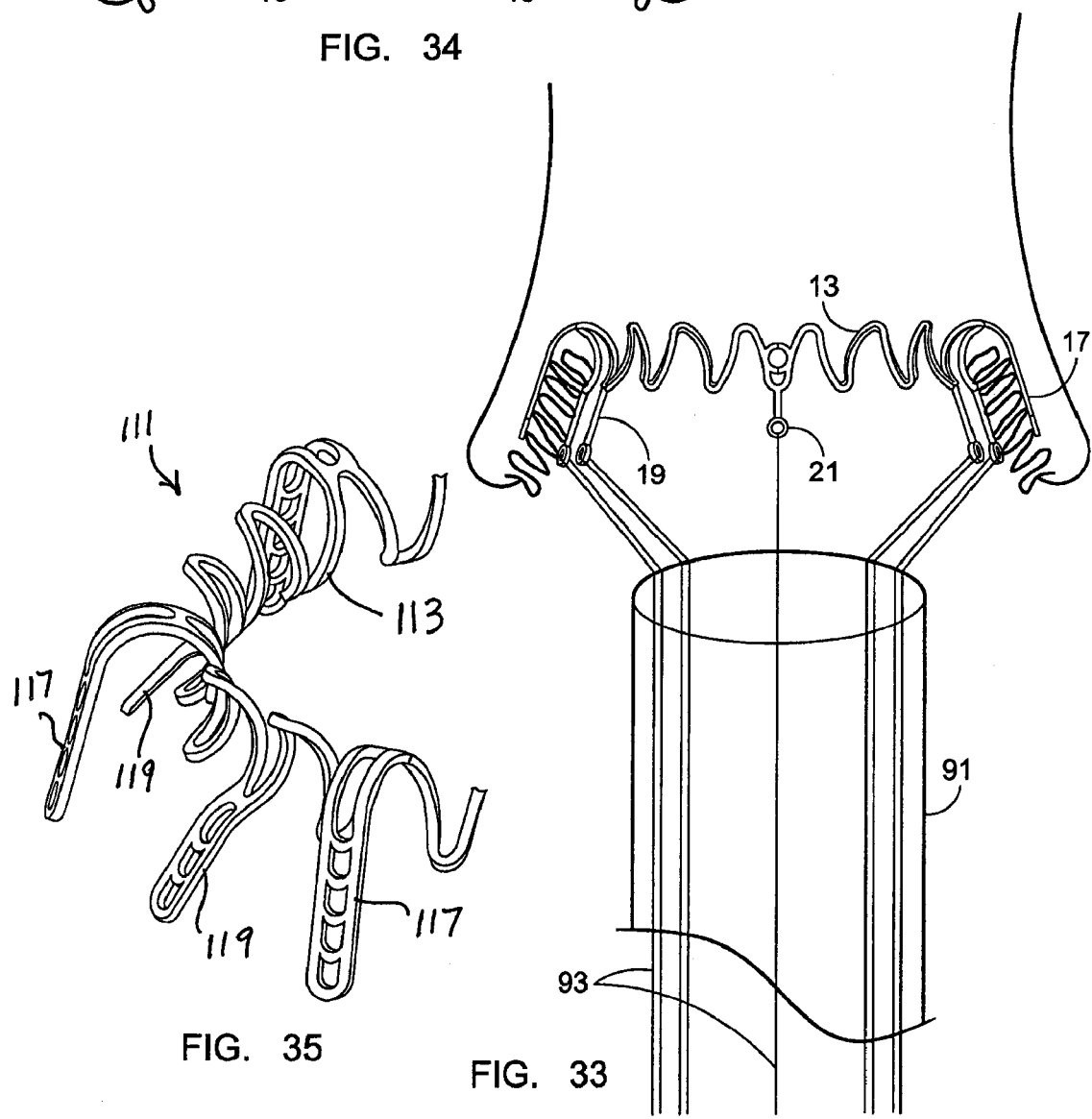
FIG. 35
FIG. 33

MINIMALLY INVASIVE HEART VALVE REPLACEMENT

CROSS REFERENCE TO RELATED APPLICATIONS

This application is a continuation of International Application No. PCT/IB2007/003850 filed 15 Feb. 2007, which claims priority from U.S. Provisional Application No. 60/774,821 filed Feb. 16, 2006, the disclosure of which is incorporated by reference.

FIELD OF THE INVENTION

The present invention relates to a prosthetic valve for implantation in the heart in a minimally invasive or percutaneous manner, and more particularly to a prosthetic heart valve suitable for replacement of a defective human heart valve, most particularly an aortic valve.

BACKGROUND OF THE INVENTION

Four valves in the heart serve to direct the flow of blood through the two sides of the heart in a forward direction. The mitral valve, located between the left atrium and the left ventricle, and the aortic valve, located between the left ventricle and the aorta, constitute the systemic portion of the heart. These two valves direct oxygenated blood coming from the lungs through the left side of the heart into the aorta for distribution throughout the body. The right side of the heart includes the tricuspid valve, located between the right atrium and the right ventricle, and the pulmonary valve, located between the right ventricle and the pulmonary artery. These two valves direct de-oxygenated blood returning from the body through the right side of the heart into the pulmonary artery for distribution to the lungs, where it again becomes re-oxygenated to begin its circuit anew.

Heart valves are passive structures having leaflets that simply open and close in response to differential pressures on either side of the particular valve. The mitral valve has two leaflets and the tricuspid valve has three. The aortic and pulmonary valves are sometimes referred to as semilunar valves because of the appearance of their three leaflets; these leaflets are shaped somewhat like a half-moon and are sometimes termed cusps.

The leaflets and surrounding elements of each valve vary with the function of the heart it supports. The atrioventricular valves, otherwise known as mitral (in the left chamber of the heart) and tricuspid (in the right chamber of the heart), are generally a continuum extending from the myocardium or muscular wall of the lower chambers, through the papillary muscles, to which is attached a confluence of tendinous rope-like elements, known as chordae tendinae, that are attached to the edges and undersurface of the differently shaped leaflets which open to allow flow and close to stop flow. The leaflets terminate at a ring-like structure usually known as an annulus, which is part of the fibrous skeleton of the heart.

When the left ventricular wall relaxes, the ventricular chamber enlarges and draws in blood from the atrium as the leaflets of the mitral valve separate, opening the valve. Oxygenated blood flows in a downward direction through the valve, to fill the expanding ventricular cavity. Once the left ventricular cavity has filled, the left ventricle contracts, causing a rapid rise in the left ventricular cavity pressure. This causes the mitral valve to close and opens the aortic valve, allowing oxygenated blood to be ejected from the left ventricle into the aorta. The chordae tendineae of the mitral valve prevent the mitral leaflets from prolapsing back into the left atrium when the left ventricular chamber contracts. The three leaflets, chordae tendineae, and papillary muscles of the tricuspid valve function in a similar manner, in response to the filling of the right ventricle and its subsequent contraction.

The cusps of the aortic valve respond passively to pressure differentials between the left ventricle and the aorta. When the left ventricle contracts, the aortic valve cusps open to allow the flow of oxygenated blood from the left ventricle into the aorta. When the left ventricle relaxes, the aortic valve cusps reassociate to prevent blood, which has entered the aorta from leaking (regurgitating) back into the left ventricle. The pulmonary valve cusps respond passively in the same manner in response to relaxation and contraction of the right ventricle in moving de-oxygenated blood into the pulmonary artery and thence to the lungs for re-oxygenation. These semilunar valves do not require associated chordae tendineae or papillary muscles.

Stenosis is one problem that heart valves may develop in which a valve does not open properly, another is insufficiency, or regurgitation, where a valve fails to close properly. In addition, a bacterial or fungal infection may require that a heart valve be surgically repaired or replaced. Sometimes such a problem can be treated by surgical repair of a valve; however, often a valve is too diseased to repair and must be replaced. If a heart valve must be replaced, there are currently several options available, and the choice of a particular type of artificial valve depends on factors including the location of the valve, the age and other specifics of the patient, and the particular surgeon's experiences and preferences.

Replacement heart valves or heart valve prostheses have been produced for more than four decades. Such valves have been made from a variety of materials of biologic and artificial nature; as a result two distinct categories of the prostheses have evolved: biological and mechanical prosthetic heart valves. Mechanical or artificial valves are typically constructed from nonbiological materials, such as plastics, metals and other artificial materials which, while durable, are prone to blood clotting which increases the risk of an embolism. Anticoagulants which may be taken to prevent blood clotting can possibly complicate a patient's health due to increased risk of hemorrhage.

Biological or tissue valves are constructed from animal tissue, such as bovine, equine or porcine tissue, although some efforts have been made at using tissue from a patient for which the valve will be constructed. Tissue valves are often constructed by sewing leaflets of pig aortic valves to a stent to hold the leaflets in proper position, or by constructing valve leaflets from the pericardial sac of cows, horses or pigs and sewing them to a stent. The pericardium is a membrane that surrounds the heart and isolates it from the rest of the chest wall structures. Such porcine, equine or bovine tissue is chemically treated to alleviate antigenicity and to make them more durable. Additional treatments may be applied to avoid structural valve deterioration in the long-term due to calcification. One main advantage of tissue valves is that they do not cause blood clots to form as readily as do the mechanical valves; therefore, they do not absolutely require life-long systemic anticoagulation. The major disadvantage of tissue valves is that they lack the long-term durability of mechanical valves.

Aortic stenosis is a very common disease of the aortic valve in the left ventricle of the heart in people above seventy years old and occurs more and more frequently as the subject gets older. When the aortic valvular orifice becomes tightly stenosed, blood can no longer be freely ejected from the left ventricle. As a result, the left ventricle has to markedly increase its ventricular chamber pressure to discharge blood past the stenosed aortic orifice; such causes a patient to have syncope, chest pain and difficulty in breathing.

Various surgical techniques that have been used to repair a regurgitant or damaged mitral valve include annuloplasty, quadrangular resection (narrowing the valve leaflets), and commissurotomy (cutting the valve commissures to separate the valve leaflets). The most common treatment for mitral stenosis and diseased aortic valve has been the replacement of an affected valve by a prosthetic valve via open-heart surgery by excising the valve leaflets of the natural valve and securing a replacement valve in the valve position, usually by suturing the replacement valve to the natural valve annulus. In instances where a patient is deemed operable only at too high a surgical risk, one alternative in valve stenosis has been to dilate the native valve with a balloon catheter to enlarge the valve orifice; however, such practice has experienced a high restenosis rate.

Generally, it would be desirable if heart valves could be replaced using minimally invasive techniques. Proposals have been made to remove a defective heart valve via an endovascular procedure, that is, a procedure where the invasion into the body is through a blood vessel, such as the femoral artery, and is carried out percutaneously and transluminally using the vascular system to convey appropriate devices to the particular body position to carry out the desired procedure. Angioplasty is also an example of such a procedure wherein a catheter carrying a small balloon at its distal end is manipulated through the body's vessels to a point where there is a blockage in a vessel. The balloon is expanded to create an opening in the blockage, and then deflated; the catheter and balloon are then removed. Such endovascular procedures have substantial benefits both from the standpoint of health and safety as well as cost. Such procedures require minimal invasion of the human body, and there is consequently considerable reduction and in some instances even elimination, of the use of a general anesthesia and much shorter hospital stays.

U.S. Pat. No. 6,168,614 to Andersen et al., the disclosure of which is incorporated herein by reference, discloses a heart valve prosthesis that can be implanted in the body by use of a catheter. The valve prosthesis includes a support structure or stent with a tissue valve connected to it that is delivered in a collapsed shape through a blood vessel. It is secured in expanded condition at a desired location in a blood vessel, e.g. downstream for the aortic valve.

Until recently, simple implantation of a valve prosthesis for the treatment of aortic stenosis without excising the native valve has been considered generally unrealistic because it was deemed difficult to simply superpose an implanted valve on the distorted stenosed native valve. More recently, however, procedures have been proposed, particularly for replacement of an aortic valve, such as those illustrated in U.S. Patent Application Publication No. 2005/0143809 to Salahieh et al., the disclosure of which is incorporated herein by reference, for endovascularly delivering an aortic prosthesis through the patient's aorta and implanting it within the confines of native valve. The prosthesis is delivered in a sheath to a location near the patient's native aortic valve and then expanded from its collapsed configuration to a deployed configuration. A variety of arrangements are described for deploying prostheses of various shapes and designs so that the prosthesis becomes implanted interiorly of the three native leaflets of the aortic valve, which are compressed radially outwardly.

Systems of this general type have shown promise and are considered to be attractive and accordingly, efforts are continuing to produce improvements in such prosthetic valves that can be minimally invasively implanted.

To repair or replace the mitral valve, a conventional procedure for approaching the left atrium has been employed by the use of intravascular catheterization from a femoral vein through the cardiac septal, which separates the right atrium and the left atrium. In some aspects, this intravascular procedure is not only dangerous and tedious because of long tortuous route, but it has limited use because of the catheter size suitable for intravascular insertion.

Overall, the use of a minimally invasive approach has a great number of advantages; an endovascular approach has generally been used. However, there is only limited space available within the vasculature; thus, the surgical field is often only as large as the diameter of a blood vessel. Consequently, the introduction of tools and prosthetic devices becomes greatly complicated, and the device to be implanted must be dimensioned and configured to permit it to be introduced into the vasculature, maneuvered therethrough, and then positioned at a desired location. In the majority of aged patients suffering from aortic stenosis, the aortic vessel and aortic arch are affected by calcified atheromatous plaques. Delivery of bulky tools and prosthetic devices retrograde through an atheromatous aortic vessel has increased risk of injuring of the atheromatous aortic wall with subsequent potential embolism and even aortic wall rupture.

Sterman et al., U.S. Pat. No. 6,283,127, the disclosure of which is incorporated herein by reference, discloses a minimally invasive system for facilitating intervention within the heart or great vessels without the need for a median sternotomy or other form of gross thoracotomy in order to try to substantially reduce trauma, risk of complications, recovery time, and pain for the patient. The surgical procedure is not endovascular, but is performed through percutaneous penetrations within intercostal spaces of the patient's rib cage, without cutting, removing, or significantly displacing any of the patient's ribs or sternum.

U.S. Pat. No. 6,869,444, the disclosure of which is also incorporated herein by reference, discloses the implantation of a prosthesis, which may include only a single leaflet for a mitral valve, through a barrel of an implantation device that is inserted either through the left atrial wall or through the apex of the heart.

U.S. Patent Application Publication No. 2005/0240200 to Bergheim, the disclosure of which is also incorporated herein by reference, discloses methods and systems for delivering a valve prosthesis to a site within the heart generally at or near the apex of the heart.

Therefore, it would be desirable to provide a delivery system for delivering a prosthetic heart valve to a patient's heart configured to be releasably folded or crimped inside a lumen of the delivery system through a percutaneous intercostal penetration of a patient's chest, or through an opening at a carotid artery, jugular vein, subclavian vein, femoral vein and other blood vessel.

SUMMARY OF THE INVENTION

It is one aspect of the present invention to provide a prosthetic heart valve with an expandable-collapsible support structure having sufficient flexibility to permit repositioning the valve after its initial placement by reversion to the collapsed stage before final placement.

The present invention provides a prosthetic valve, which is particularly designed for minimally invasive implantation into the heart through the apex of the heart. The apex of the heart is the blunt-rounded, inferior extremity of the heart formed by the termini of the left and right ventricles, and in normal healthy humans, it generally lies behind the fifth intercostal space, left from the mid-sternal line.

The anatomical structure of the apex permits the introduction of various surgical devices and tools into the heart without significant disruption of natural mechanical and electrical heart function. By using such direct access to the heart through the apex, severe size constraints which have been a limitation of endovascular surgical methods of repair/replacement are avoided. In other words, whereas access through the femoral or other vessels in percutaneous endovascular methods are limited to the diameter of the vessel (approximately 8 mm), access through the apex may reasonably avail itself of an opening as large as about 25 mm. Such access to the heart permits greater flexibility with respect to the construction and delivery of a prosthetic valve for minimally invasive delivery.

The present invention further provides an envelope or anchoring device that may be separate from or part of the collapsible-expandable heart valve; it is formed with distal and proximal sections and is made of a shape-memory material. The design is such that, after the envelope has been inserted through the orifice of an aortic or other valve, a distal section of it everts and wraps around the free ends of the aortic leaflets so as to eventually seat against the aortic or downstream surface of the leaflets, while a main body section expands radially outward and a proximal section swings radially outward to seat against the ventricular or upstream surface of the aortic leaflets. This effectively sandwiches the leaflets between the juxtaposed envelope sections, firmly implanting the envelope at the desired location within the orifice of the defective aortic valve. The implanted envelope thus serves as an anchor for a collapsible-expandable heart valve, which may be separately implanted as a second step and secured thereto via interengaging means provided on the envelope and on a stent portion of the prosthetic heart valve. Alternatively, the envelope can be incorporated as a part of the heart valve stent to allow a single-step implantation.

In a further aspect, the invention provides a method for anchoring a replacement valve within the confines of a diseased native valve in a minimally invasive fashion in the human heart by percutaneously entering the heart through the apex of the heart via an intercostal penetration of the chest.

In one particular aspect, the invention provides a percutaneously implantable replacement heart valve, which valve comprises an outermost envelope portion of shape-memory material for sandwiching the native leaflets of a stenotic valve between parts thereof, a collapsible-expandable heart valve stent of generally tubular shape which includes proximal and distal rings and at least three spaced apart posts that extend axially between said rings, and a valvular device comprising a plurality of flexible leaflets disposed interior of said stent, which leaflets open to permit blood flow in a downstream direction and close to prevent blood flow in an upstream direction therethrough.

In another particular aspect, the invention provides an anchoring device for securing a percutaneously implantable replacement heart valve in an existing valve in the human heart, which device comprises a framework of generally tubular shape which is constructed of shape-memory material and which has a portion which everts as a result of temperature change and wraps about the native leaflets of a stenotic or malfunctioning valve when positioned in the orifice of such valve, said framework including a central portion, a distal portion and a proximal portion that are integral with one another, and said distal portion of said framework having a memory such that, upon transition to the temperature of the human body, it everts so as to wrap around the free ends of native leaflets of the valve to contact downstream surfaces of the valve leaflets and secure said framework within the human heart valve.

In a further particular aspect, the invention provides a minimally invasive method for percutaneously implanting a replacement heart valve in the orifice of a native valve within the human heart, which method comprises providing an intercostal opening in the chest of the patient and an adjacent opening in the apex of the human heart, inserting a first catheter through said openings and through a ventricle of the heart to the location of a diseased valve, deploying a generally tubular anchoring device of shape-memory material from the distal end of said catheter at a location generally interior of the native valve, locating said anchoring device so that, when its shape-memory causes a distal portion thereof to evert, said anchoring device wraps itself around and about the free ends of the native valve leaflets, allowing a central portion of the anchoring device to expand to a greater diameter within the orifice of the native valve and sandwich the leaflets between it and the everted portion, removing the first catheter and inserting a second catheter that includes a replacement valvular device that incorporates an expandable stent loaded on a delivery implement, causing said replacement valvular device to be deployed distally from the open distal end of the catheter, locating the replacement valvular device interior of said implanted anchoring device and allowing the stent to expand in diameter and mate with said anchoring device, and withdrawing the catheter and delivery implement and closing said openings in said heart and the chest of the patient.

BRIEF DESCRIPTION OF THE DRAWINGS

FIG. 1 is a perspective view showing framework embodying various features of the present invention that is included in an anchoring device or encapsulation envelope for a replacement heart valve, which framework is illustrated in its collapsed orientation.

FIG. 2 is a perspective view of the framework of FIG. 1 in an intermediate expanded orientation.

FIG. 3 is a perspective view of the framework of FIGS. 1 and 2 shown in its final "memory" orientation.

FIG. 4 is a front view of the framework shown in FIG. 3.

FIG. 5 is a perspective view of a stent for a replacement heart valve shown in its fully retracted or collapsed orientation.

FIG. 6 is a perspective view of the stent of FIG. 5 shown in its expanded orientation.

FIG. 7 is a view similar to FIG. 6 showing an alternative embodiment of a stent for a heart valve which incorporates an anchoring device portion and embodies various features of the present invention.

FIG. 8 is a cross-sectional view taken generally along the line 8-8 of FIG. 7.

FIG. 13 is a schematic view showing the anchoring framework of FIG. 1 for an encapsulation envelope loaded onto a delivery implement, with the biologically compatible sheet material that would cover the framework to complete the envelope omitted for clarity.

FIGS. 14, 15, 16, 17 and 18 are schematic views showing successive stages of the implantation of the anchoring framework of FIG. 1 of such an encapsulation envelope within the orifice of a malfunctioning aortic valve.

FIGS. 25 and 26 are schematic views showing patterns of looped string that may be used to control the expansion or to effect the subsequent collapse of a flexible ring of shape-memory material such as those which form parts of the structures depicted in FIGS. 2 and 6.

FIGS. 27 and 28 are perspective views of an alternative embodiment of an anchoring device embodying various features of the invention, shown in its tubular deployment orientation and in its folded memory orientation.

FIG. 29 shows the collapsed framework for an encapsulation envelope as illustrated in FIG. 1, disposed within a catheter near the distal end thereof with a set of loops of string attached only to the eyelets at the ends of the proximal arms.

FIG. 30 is a schematic perspective view similar to FIG. 29 showing the loaded catheter positioned centrally within a defective aortic valve of a patient.

FIG. 31-33 show a succession of steps where the framework of the encapsulation envelope is caused to emerge from the distal end of the catheter and then change in shape, driven by its shape-memory, so as to encapsulate the tip portions of the aortic valve leaflets as the catheter is withdrawn proximally.

FIG. 34 shows the encapsulation envelope in place, following the cutting of the loops of string and withdrawal of the catheter, ready to accept implantation of a heart valve as depicted in FIGS. 22-24.

FIG. 35 is a fragmentary perspective view of an alternative embodiment of a framework for an anchoring device similar to that shown in FIG. 1.

DETAILED DESCRIPTION OF THE PREFERRED EMBODIMENTS

Figure 9:
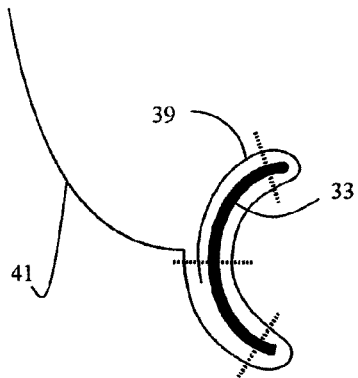
FIGS. 9 and 10 are schematic views illustrating how a flexible leaflet may be attached to one ring portion of the heart valve stent of FIG. 6.

A first preferred embodiment of an anchoring framework structure 11 for an encapsulation envelope or anchoring device incorporating various features of the invention is shown in FIGS. 1 through 4. The framework has a tubular shape and is designed for anchoring a replacement heart valve at the location of a diseased native valve without excising the native valve. The encapsulation envelope has a tubular deployment form and includes this framework 11 surrounded with a covering layer of biocompatible thin sheet material (not shown). It is designed to be deployed in a collapsed condition using a delivery implement where it is slidably disposed within a catheter that is caused to enter the body through a cannula implanted intercostally in the chest, through which it is directed through the apex region of the heart and, for example, into the left ventricle, and then through the orifice of the aortic valve.

The encapsulation envelope framework 11 is made of wire-like material, which may be of circular, square, rectangular, oval or other cross section, of a shape-alloy material which has sufficient elasticity such that it can be manually crimped or contracted by applying radially inward directed forces to reduce the diameter of the tubular structure. More specifically, the framework 11 is preferably made of a suitable metal or polymeric material that is biocompatible and has shape-memory properties. However, it is more preferably made of a Nitinol alloy that has an activation temperature (Af) below normal body temperature of about 37° C.; thus, the radial force it will exert in tending to return to its "memory" shape can be controlled by varying the temperature difference between the Af and the temperature at which it will be deployed. The individual elements of the overall filamentous construction will usually have a square, rectangular, round or oval cross section that results from polishing after the structure has preferably been laser-cut from a single tube having an appropriate diameter proportional to the desired final valve size. After such cutting, the framework is formed to take its ultimate desired final shape and then treated with heat to set its "memory" so it will always return to this shape. By appropriately selecting a Nitinol alloy and processing it, the framework 11 will have superelastic properties at and below normal body temperature so it will exhibit sufficient flexibility to allow it to be manipulated. Accordingly, as the implanted encapsulation envelope gradually warms to body temperature, the framework 11 slowly assumes its desired folded-over final shape which is shown in FIGS. 3 and 4.

More specifically, the envelope framework 11 is formed with a central ring portion 13 of generally undulating shape having a plurality of loops 15 arranged in generally sine wave fashion and extending in opposite directions. Such constructions are relatively common in stents for biological heart valves; see for example U.S. Pat. No. 6,168,614, the disclosure of which is incorporated herein by reference. Extending in both directions from selected tips of the loops 15 are a plurality of arms 17 and 19, as best seen in FIG. 2; there are preferably at least 3 of each arms, more preferably at least four of each arms, and still more preferably at least six of each. Although all of the loops 15 could have an arm projecting from the tip thereof, the construction is preferably such that distally extending arms 17 and proximally extending arms 19 are arranged to alternate around the perimeter of the illustrated envelope ring 13, with every third proximally extending loop having an arm 19 projecting therefrom and with every third distally extending loop having a distally extending arm 17 projecting therefrom.

A small tab 21, which is apertured to form a circle or eyelet, is formed integrally with the end of each arm 17, 19 to spread the force which it applies across the surface area of the aortic leaflet with which it will ultimately be in contact. These circular tabs 21 can serve as eyelets through which a control string arrangement may be removably connected to the framework of the envelope to facilitate the installation of the envelope within the orifice of the native valve which it is to replace. Moreover, there are also multiple, in particular three, circular eyelets 23 incorporated in the central ring 13 that are equiangularly spaced from one another (i.e. at 120°); they are each strategically positioned between the legs which form one of the loops which has a proximal arm 19 at its tip, as best seen in FIG. 3. These three eyelets 23 may also serve as connectors through which similar strings or chords can be routed for controlling the expansion or for subsequently causing contraction of the central ring portion 13 of the superelastic envelope framework.

Pursuant to the foregoing, the framework 11 would be laser-cut from a single tube of Nitinol alloy and polished. It would then be shaped to have the desired final shape shown in FIGS. 3 and 4, where both sets of arms 17 and 19 extend proximally of the central ring 13. The central ring 13 is formed to have a convex inward or interior surface that is, in essence, a section of a torus. This arrangement facilitates not only the secure implantation of the envelope in its wrapped-around orientation about the aortic leaflets, but it provides an interengagement surface that is employed to anchor the stent of the valvular device, e.g. bioprosthetic heart valve, that will regulate flow through the orifice.

Illustrated in FIGS. 5 through 6 is a preferred embodiment of a tubular stent 29 that is designed to be incorporated as a part of a bioprosthetic heart valve having a shape that will mate with the framework 11 of the implanted envelope just described which will serve to anchor the heart valve in place. The tubular stent 29 is similarly made of shape-memory material and is constructed to allow it to be expanded and/or contracted to exhibit different diameters. Basically, the stent 29 includes a distal or apical ring 31 and a basal or proximal ring 33, with multiple, in particular three, longitudinally extending posts 35, the ends of which are incorporated into these two, spaced-apart ring portions of the stent. The posts 35 are located equiangularly at 120° to one another. The ring portions and the posts may be formed of generally wire form material as described hereinbefore with respect to the envelope; however, the stent 29 is again preferably cut from a tube. Both rings are again of undulating design, with the proximal ring 33 preferably having slightly deeper loops. Circular apertures 37 are provided near each end of the three posts; these facilitate the routing of control cords or strings as mentioned hereinbefore with respect to the central ring structure 13 of the envelope. The stent 29 is likewise more preferably laser-cut from a tube of shape-memory metal alloy.

Figure 11:
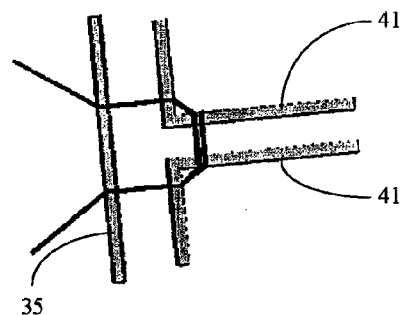
FIGS. 11 and 12 are fragmentary schematic views showing how individual flexible leaflets may be attached to post portions of the stent and to one another by thread or cords.
Figure 10:
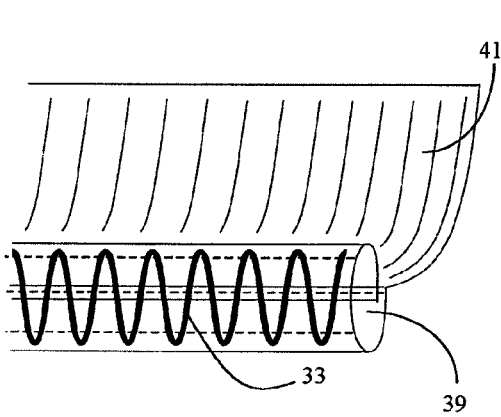
Figure 12:
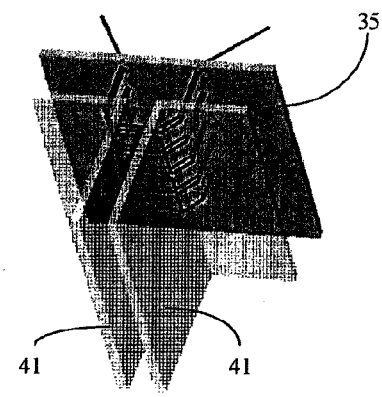

To provide leaflets for the valvular device, flexible sheet material 39, e.g. pericardium, is wrapped around sections of the proximal or basal ring structure 33 to completely surround the ring portions between the posts 35 so that it extends distally interior of the ring within the stent 29 to form the leaflets 41, as shown schematically in FIGS. 9 and 10. The proximal or basal ring 33 of the stent is formed, as can be seen in FIGS. 6 and 9 to have an outwardly concave C-shape contour. It essentially defines a partial toroidal surface as its circumference, and such is matched to the interior surface of the central ring 13 of the envelope framework 11 with which it mates. The posts 35 have rows of parallel apertures 43 extending throughout their length through which chords or ties 45 are passed, as shown schematically in FIGS. 11 and 12, to secure lateral edges of the leaflets 41 in place within the interior of the stent 29 to create a working valve. Any suitable leaflet designs and attachment may be employed, such as those well-known in this art; for example, a preferred pattern of threading such as that shown in FIG. 12 may be used to secure the side edges of three leaflets to one another. In general, leaflets of any of the general types shown in the following three Published U.S. Applications may be used: Nos. 2005/0075731; 2005/0113910; and 2005/0203617, the disclosures of which are incorporated herein by reference. If desired, pledgets can be provided to reinforce the leaflets 41 where there is attachment to the posts.

To implant the encapsulation envelope, a small, lateral thoracotomy is performed in the appropriate lateral intercostal space where the apex of the heart is located, and a tubular access cannula or tube with an internal trocar or mandrel is inserted into the retracted incision. Purse-string sutures are placed about the apex of the heart and used to secure the cannula in place so that it provides blood-tight access into the heart. For replacement of an aortic valve, aortic stenosis is first visualized using contrast (aortography) and radiography or transesophageal echocardiography.

A dilation balloon is generally first inserted through the access cannula and used to dilate the stenotic valve. The diameter achieved through such dilation is measured, using contrast in the dilation balloon and aortography. Based upon these measurements, an encapsulation envelope having a framework 11 of the appropriate size is selected, and such is loaded into a delivery catheter in tubular form. The envelope framework 11 in its tubular deployment form as shown in FIG. 1 is positioned about the exterior surface of a tubular delivery implement 47, and the assembly is loaded into the distal end of a catheter (not shown). As depicted schematically in FIG. 13, at three spaced apart locations along the length of the implement 47, three separate sets 49a, 49b and 49c of strings are routed through the open upper end and two longitudinal sets of openings. At each longitudinal location, loops of string may emanate from three or more entry points in the tubular wall that are spaced circumferentially about the tubular surface of the implement. These sets of strings 49 are respectively slidably routed through the three sets of eyelets 21 and 23 emanating from the three different, longitudinally spaced regions of the envelope framework 11.

With the implement 47 and the crimped, compressed envelope framework 11, which is supported on its outer surface, slidably disposed within the surrounding outer catheter sleeve, the catheter is inserted through the cannula and maneuvered into the left ventricle of the heart, until the distal end of the catheter sleeve reaches the vicinity of the aortic valve 51. Then the delivery implement 47 is extended distally so that it emerges from the end of the catheter sleeve, and it is positioned at a location within the center of the aortic valve. At this point, the first set of strings 49a that are connected to the ends of the distal arms 17 are released in a controlled manner to allow the distal arms 17 of the envelope framework 11 to begin to extend radially outward, as generally illustrated in FIG. 14, pursuant to their "memory." There may be six loops or three loops (with each one passing through two eyelets) of string 49a which emerge through the open upper end of the implement; these may be separate loops or all may be part of one continuous length of string. In either instance, the proximal ends of the loops are preferably connected to a ratchet mechanism that facilitates controlled release or rewinding. Once the arms 17 have reached the orientation shown in FIG. 15 where their tips extend radially beyond the tips of the leaflets 53, the implement 47 may be pulled back proximally to some extent. The arrangement at the proximal end of the implement 47 (and the catheter), exterior of the human body, is preferably such that each group of loops of string emanating from a particular longitudinal region of the implement 47 is controlled by a separate ratchet; differential passage of string lengths for each of these individual sets 49a, 49b and 49c is thus possible. This facilitates the desire to allow little or no expansion of the central ring portion 13 or outward movement of the proximal arms 19 of the framework until the original distal arms have everted. Upon such eversion, these arms 17 of the envelope framework will have assumed an orientation extending proximally at about a 45° angle to the axis of the implement, as shown in FIG. 16.

Figure 17:
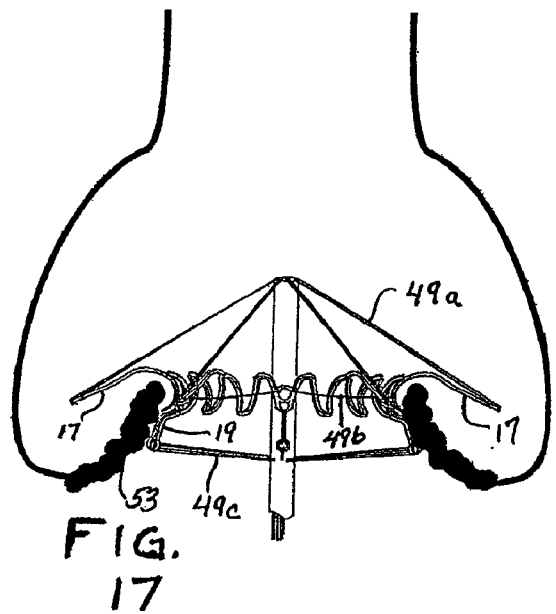
Figure 18:
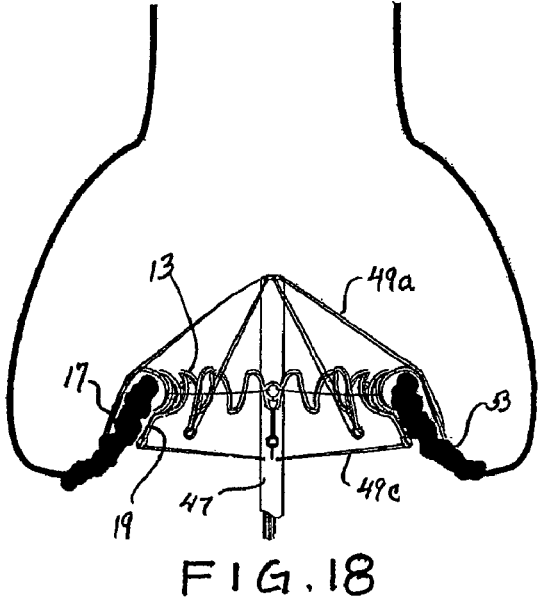

When this orientation has been reached and the catheter and/or delivery implement 47 are pulled back proximally so that the ring section 13 is in general alignment with the tips of the leaflets 53, and the arms 17 are now hooked around the free ends of the leaflets 53, as seen in FIG. 16, the second set of strings 49b at the central region, which are attached to eyelets 23 in the ring portion 13 of the envelope, are released. The ring portion 13 now expands radially outward to entrap the free ends of the leaflets 53 in the bights formed therewith by the everted arms 17, with its outwardly concave, C-shaped surface contacting the ventricular surfaces of the leaflets. Finally, the third set of strings 49c controlling the proximal arms 19 are released; this allows these arms to follow their shape-memory and swing outward as shown in FIG. 17 so they abut the ventricular surface of the leaflets. Continued movement of both sets of arms sandwiches the leaflets 53 between the two sets of arms, which are located alternately on opposite surfaces of the leaflets, as depicted in FIG. 18. At this point, all of the expansion steps can still be reversed by simply pulling the loops of strings back through the entry points into the implement 47 in the opposite order; this will again collapse the superelastic framework material of the envelope should it be felt that the location of the encapsulation envelope is not precisely correct.

On the assumption that the exact desired location has been achieved, one arm of each loop of string is cut at a location outside the body, and the strings are removed by pulling out the other arm of each loop of string, leaving the envelope in place (the framework of which has now reached its "memory" orientation shown in FIGS. 3 and 4), as depicted in FIG. 18. At this point, a temporary valve 55 may be deployed.

Figure 19:
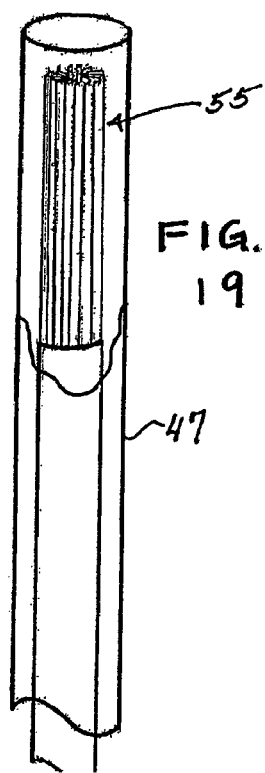
FIG. 19 is an enlarged perspective view of the delivery implement of FIG. 13, following its delivery of the encapsulation envelope, with a portion broken away to show a temporary valve positioned in the lumen thereof near its distal end.
Figure 20:
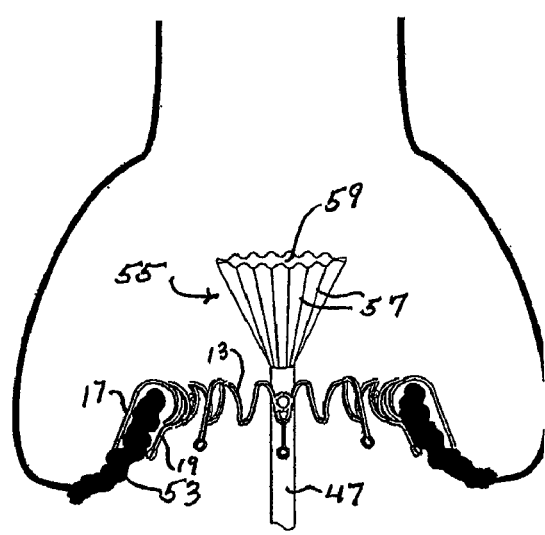
FIGS. 20 and 21 are schematic views showing the temporary valve of FIG. 19 during systole and diastole as it functions in combination with the encapsulation envelope that has been implanted in the aortic valve.
Figure 21:
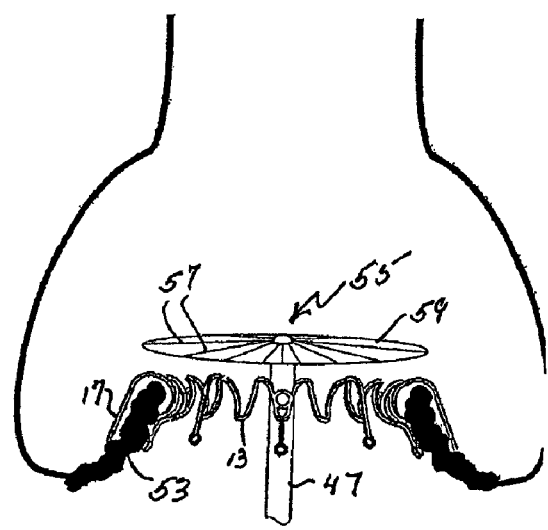

Such a valve might be originally loaded internally of the tubular delivery implement 47 in tandem with the envelope which is located on its exterior surface. An exemplary umbrella-like valve is illustrated in FIG. 19 as having been advanced to a location near the distal end. The valve 55 has a plurality of straight ribs 57 that extend radially outward from a center core and that are lightly spring-loaded to a radially extending orientation. The ribs 57 support a circular panel 59 of flexible film which serves as a temporary valve so long as the implement 47 and the catheter are in position in the heart. The valve is pushed from the distal end of the delivery implement 47 by a suitable flexible pusher 56 which slides within the implement 47. FIG. 20 depicts the umbrella-like temporary valve 55 in its open, slightly compressed orientation during systole as blood flows through the aortic orifice. FIG. 21 shows the circular valve 55 near its closed position during diastole when it generally blocks blood from the aorta from regurgitating into the left ventricle.

Figure 22:
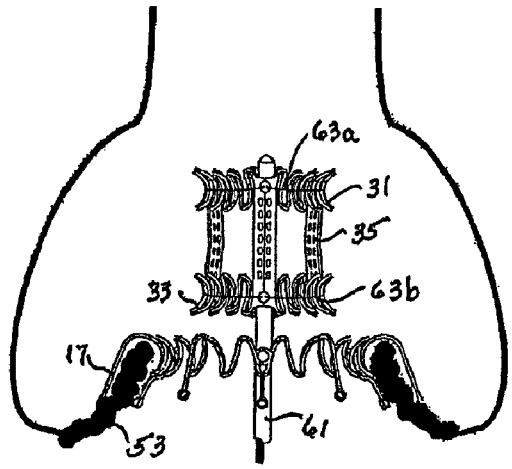
FIGS. 22, 23 and 24 are schematic views showing successive stages of (a) delivering a replacement heart valve (with its leaflets omitted for clarity) to the aortic valve of a patient in which the anchoring framework of FIG. 1 has been implanted and (b) then interengaging the stent of that heart valve with the implanted framework of the encapsulation envelope.

When the envelope framework 11 has been implanted and a correctly sized valvular device has been chosen, the valvular device is installed on a similar deployment device or delivery implement 61, and it is loaded within a surrounding catheter sleeve. When all is ready, the temporary valve 55 is withdrawn back within the implement 47 that is presently still residing in the aortic valve orifice, and the catheter sleeve and implement are withdrawn. The new catheter carrying the replacement valvular device is now delivered through the cannula and into the left ventricle of the heart. Once in position in the left ventricle, the implement 61 carrying the valvular device is deployed from the delivery catheter at a location in the aortic region on the aorta side of the encapsulation envelope 11 that was earlier implanted, as depicted in FIG. 22, where the stent of the valvular device is shown, the interior leaflets being omitted for clarity. The stent 29 is supported on the delivery implement 61 by two sets of looped strings 63a and 63b similar to those which were earlier described. Then, by observing using radiography or transesophageal echocardiography, precise positioning of the delivery implement 61 is achieved by maneuvering its flexible tip. Once in the exact desired position so that the C-shaped cross-section basal ring 33 of the valve stent 29 is aligned with the C-shaped central ring 13 of the implanted envelope 11, the distal and proximal rings 31, 33 of the stent portion are permitted to expand radially outward by controlled releasing of the sets of strings 63a and 63b.

The stent 29 is constructed so that the curvature of the basal ring 33 very closely matches the convex curvature of the interior surface of the central ring portion 13 of the implanted envelope; if desired, the shape-memory can be employed to accentuate this curvature. As a result, a self-centering effect is achieved, with the basal ring 33 of the valve stent 29 securely interengaging with the ring 13 of the already implanted encapsulation envelope 11 as the two rings 33 and 13 nest together; simultaneous expansion of both rings 31, 33 of the stent 29 is permitted by releasing the restraining sets of strings 63a and 63b at the same time. The two respective curvatures are preferably selected such that a very slight central annular gap is left through which the string loops 63b that are used to control the expansion-contraction of the basal ring of the heart valve stent can slide.

Figure 23:
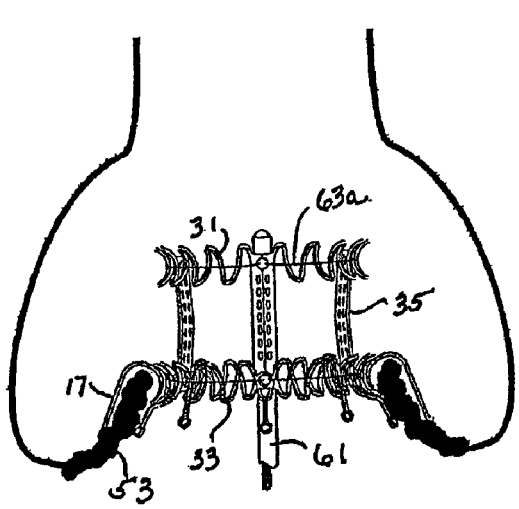
Figure 24:
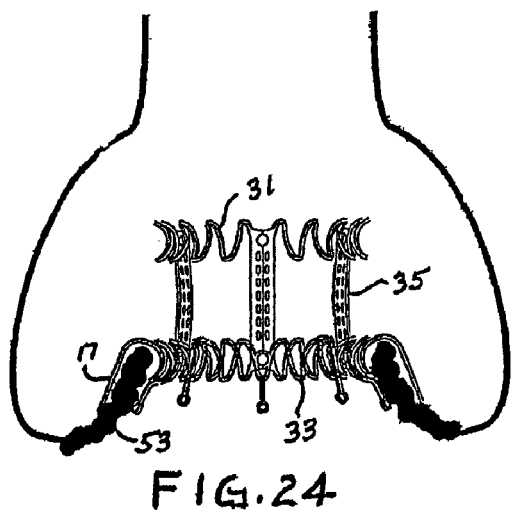

When such positioning and the shape-memory expansion has been completed, as shown in FIG. 23, the function of the valve is observed by radiography or by transesophageal echocardiography. Should the valve position not be completely satisfactory, the two sets of looped strings 63a, 63b attached to the basal ring 33 and the apical ring 31 of the stent can be pulled to collapse the flexible stent 29 sufficiently to allow the valvular device to be repositioned or even to be completely collapsed and then removed.

Once the final desired placement and mating of the valvular device within the outer encapsulation envelope has been achieved, the delivery implement 61 is removed; however, the loops 63 of string that extend through the catheter are preferably temporarily left in place. Valve function and effective orifice area are then observed by radiography or the like, and should it be felt that the orifice of the implanted valve is too small, the strings 63 are conveniently used to advantage to guide a dilation balloon into place within the interior region of the basal ring portion 33 of the stent. With the dilation balloon located interior of the basal ring 33 of the stent, it is inflated to dilate this portion of the stent only; this causes both the basal ring and the envelope framework ring 13 with which it is firmly nested to be simultaneously slightly radially expanded, such being made possible as a result of their undulating constructions. The balloon is withdrawn once the final diameter of the valve has been determined to be satisfactory, and the sets of strings 63a and 63b are cut at one arm of each loop and pulled out via the other arm.

Disclosed in FIGS. 29-34 is an alternative procedure for implanting an anchoring device having a framework 11 of the construction shown in FIG. 1 within the orifice of a malfunctioning aortic valve; this procedure might be employed instead of the implantation procedure described with respect to FIGS. 13-18. In comparison to the earlier described procedure, this procedure employs a catheter 91 and only a single set of strings, i.e. loops 93 that pass through the eyelets 21 that are located at the ends of the proximal arms 19. Instead of employing a delivery implement 47 about which the envelope framework 11 is disposed in surrounding relationship, the envelope framework 11 is loaded into the proximal end of the catheter 91 with the one set of string loops 93 attached, and it is moved to a location near the distal end of the catheter by a pusher (not shown) similar to that previously mentioned for pushing the temporary valve 55 from the interior of the delivery implement 47.

FIG. 29 shows the crimped, compressed envelope framework 11 disposed within the distal end of the catheter 91, with one set of loops 93 of string attached which pass through the eyelets 21 at the ends of the proximal arms 19 of the framework. The catheter 91 with the encapsulation envelope loaded therein is moved into position within the center of the aortic valve, i.e. to the location as generally depicted in FIG. 30. Relative movement of a tubular pusher or piston (not shown) and the catheter 91 is then used to effect the emergence of the framework 11 from the distal end of the catheter. For example, while the pusher supports the framework 11, the catheter sleeve 91 is withdrawn proximally a sufficient distance so that the plurality of distal arms 17 are now entirely exterior of the distal end of the catheter, as shown in FIG. 31. Alternatively, the catheter 91 can be initially located as shown in FIG. 31, and the pusher used to cause the emergence of the arms 17 of the framework from its distal end.

The arms 17, which are no longer confined by the surrounding catheter sleeve and which are warming to body temperature, begin to return to their original shape as caused by their shape-memory. This causes the arms 17 to evert initially to a generally horizontal orientation, as shown in FIG. 32 where the tabs 21, at their distal ends, extend past the tips of the native valve leaflets 53. As the arms 17 continue to evert, the catheter 91 may be pulled back slightly so that the arms hook around the tips of the leaflets, and relative movement of the catheter and the pusher then causes the entire envelope framework 11 to emerge from the distal end of the catheter, with just enough tension being maintained on the set of string loops 93 to position the distal arms 17 in contact with the aortic surfaces of the leaflets 53.

Once the entire framework 11 is no longer confined at all by the catheter sleeve, and with the arms 17 now slightly hooked around the free ends of the leaflets 53, the ring portion 13 begins to expand radially outward to entrap the free ends of the leaflets in the bights formed therewith by the everted arms 17, as depicted in FIG. 33. The proximal arms 19 are now allowed to follow their shape-memory by relaxing tension on the string loops 93 so that they swing outward where they contact the ventricular surfaces of the aortic leaflets and sandwich the leaflets 53 between the two sets of arms, as earlier described. This orientation is essentially shown in FIG. 33; and the location of the envelope framework 11 is then confirmed using radiography or the like. If the exact desired location has been achieved, one arm of each loop 93 of string is cut at a location outside the body, and the strings are removed by pulling out the other arm of the string loop, leaving the encapsulation envelope of which the framework 11 is a major part, in place, as depicted in FIG. 34.

If before cutting the loops of string 93 it should be found that the desired location within the aortic valve had not been obtained, although it is not possible to realign or reposition the framework 11, the encapsulation envelope can still be withdrawn from the aortic valve so long as the loops 93 are attached. By distally advancing the catheter 91 while simultaneously pulling on the set of strings 93, the elastic proximal arms 19 are pulled away from the valve leaflets 53. Continued simultaneous gentle advancement of the catheter and pulling on the loops causes the eyelets 21 and then the arms 19 to be pulled back within the open end of the catheter sleeve and the ring portion 13 to be reduced in diameter. Once the major portions of all the proximal arms 19 are within the catheter sleeve, pushing the tubular pusher and the catheter distally through the valve region into the aorta causes the valve leaflets 53 to slip out of the bight between the everted distal arms 17 and the ring 13 of the anchoring envelope. Once this occurs, further response to the shape-memory of the distal arms 17 is such that they continue to evert further and wrap tightly onto the outer surface of the catheter sleeve 91 because the framework 11 is preferably originally set to orient the arms 17 to such a more radially inward attitude. Because the final outer diameter of such a framework 11 is essentially that of the central ring portion 13, which now extends only slightly beyond the catheter sleeve, the catheter 91 with the distal arms 17 juxtaposed about its outer surface, can be withdrawn through the cannula and taken out of the body. Here it can either be reshaped for a second installation try or replaced by another fresh encapsulation envelope.

As an alternative to using a separate envelope that is initially implanted and then used to subsequently anchor a valvular device in position within an aortic valve or the like, a combination of a heart valve stent and a framework of arms that will wrap around leaves of a malfunctioning valve can be constructed. A structure 67 of this type is illustrated in FIG. 7. The combined stent/envelope framework 67 resembles the heart valve stent 29 in that it includes three similar posts 69 that extend between and form integral parts of a distal or apical ring 71 and a basal or proximal ring 73. It would support three flexible leaflets (not shown) as described hereinbefore. Each of the rings is formed, as before, of a series of sine-wavelike loops. However, the construction is such that a plurality of distal arms 75 extend from certain of the spaced apart tips of the basal ring 73 that resemble the arms 17, and a plurality of proximal arms 77 extend in the opposite direction from other loops of the basal ring, which arms resemble the arms 19 previously described with regard to the envelope 11. Apertured tabs or eyelets 79 at the ends of both sets of arms 75, 79 again provide locations for the routing of sets of strings that are used, as explained hereinbefore, to control or reverse the shape-memory movement of the arms. A replacement heart valve incorporating the combined stent/envelope structure 67 would be loaded onto a delivery implement that includes four sets of longitudinally spaced openings, through which four sets of control strings could be routed to sets of eyelets located at spaced apart locations along the length of the structure 67. After the orifice of a malfunctioning valve has been dilated, the heart valve incorporating the combined structure 67 could be implanted using a procedure closely patterned after that already described. Because only one step would be required, there would be no need to position a temporary valve within the implantation device for use during the interim period between the two separate steps, as previously described.

Example of Detailed Surgical Protocol for Implantation of a Valve

An anesthetized patient is intubated with a single lumen tracheal tubus and arranged so that the patient is lying on his back, slightly twisted in a right lateral position with the left arm elevated to expose the left lateral thorax and to widen the intercostal space. The patient is anticoagulated with Heparin 10.000 IU/kg. A small lateral thoracotomy, having a length of about 5 cm, is performed in the $4^{th}$ or $5^{th}$ lateral intercostal space, where the apex of the heart should be located. The intercostal space is opened, and the region is retracted to achieve an opening of approximately 5×5 cm. A double lumen tubus and separate ventilation of the lungs should not be necessary, because the apex of the heart should be touching the inner thoracic wall so that it will be directly accessible in the intercostal space.

A purse string 3-0 prolene suture, reinforced with pledgets, is placed around the apex of the heart, and an incision is made at the apex of the heart. A tubular access tube or cannula with an internal trocar or mandrel is inserted into the incision at the apex of the heart. The purse-string suture is tied over ear portions of the cannula to secure it in position before the trocar is removed. The cannula provides blood-tight access into the heart. Blood from remaining bleeding is aspirated, cleaned, and returned to the patient. The cannula positioned at the apex of the heart provides a three dimensional axis about which all devices to be inserted are maneuvered.

All subsequent procedures are carried out by passage through the blood-tight cannula, and it is recommended to insert all devices during systole, while ventricular pressure is highest in the left ventricle so as to avoid the entry of air through the cannula into the left ventricle. At end of diastole, the left ventricular pressure can theoretically be negative, and as a result, it might create suction that would increase the risk for air emboli. A heart experiencing an aortic stenosis has an increased end-diastolic pressure; thus, there is practically no risk of negative pressure in the left ventricle that would draw air through the cannula.

The native aortic valve and all maneuvering of devices, placement of devices, dilation, removing of devices and removing of strings are preferably continuously visualized and observed by using radiography or transesophageal echocardiography. Contrast to facilitate radiography or transesophageal echocardiography is given through the cannula while carefully avoiding air embolism.

The aortic stenosis is visualized using contrast (aortography) and radiography or transesophageal echocardiography During systole, aortography will show the stenosis of the aortic valve. A dilation balloon is inserted through the access tube and used to dilate the stenotic valve. The achieved diameter is measured using contrast in the dilation balloon and aortography, and the aortic root and the stenotic aortic valve are measured using transesophageal echocardiography. Based upon these measurements, an appropriate size encapsulation envelope is chosen.

A catheter containing the crimped encapsulation envelope or anchoring device having the framework 11 on a delivery implement 47 is inserted through the cannula. Under control by radiography or transesophageal echocardiography, the tip of the catheter is passed through the aortic valve orifice 51 where it is positioned for delivery of the encapsulation envelope.

The C-channel central ring section 13 of the encapsulation envelope framework is placed distal of the aortic orifice. The set of strings 49a holding the distal arms 17 in the delivery orientation are released under control by transesophageal echocardiography or radiography. As a result, the distal portion of encapsulation envelope framework 11 everts, with the arms 17 folding over the aortic surfaces of the aortic valve leaflets 53 somewhat like an umbrella collapses. By then pulling the encapsulation envelope framework 11 slightly back proximally to move the central ring 13 into the aortic orifice, the folding distal arms 17 will hook about the free end portions of the aortic leaflets 53, thus encapsulating the calcified and/or cracked aortic valve leaflets by bearing against the aortic surfaces thereof. Subsequently, the set of strings 49b controlling the C-channel ring will be released, allowing it to expand so the outwardly convex C-channel central ring contacts the ventricular surfaces of the aortic valve leaflets. Finally the strings 49c routed through the tabs 21 of the lower or proximal arms 19 will be released, allowing these arms to swing outward and also contact the ventricular surfaces of the aortic valve leaflets; this sandwiches the calcified and/or cracked aortic valve leaflets 53 between the arms 17 and 19 and securely anchors the encapsulation envelope within the aortic valve orifice.

All these steps of the delivery can be undone, by tightening the strings in the reverse order to again crimp the arms 19 and the C-channel ring portion 13 back to reduce its diameter to its initial orientation on the delivery implement and extend the distal arms 17, so as to allow the envelope to be repositioned or even completely removed. Once placement and positioning are ascertained to be accurate, one arm of every string loop is cut, and each string is pulled out via the other arm. Following this step, the envelope can no longer be removed as it warms to body temperature and tightly grips the leaflets 53. The hollow delivery implement 47 for the encapsulation envelope also internally carries a temporary valve 55 in the form of a ribbed circular disc 59, that is unfolded at the tip of the implement; this temporary aortic valve 55 makes the orifice competent during diastole so long as the implement is kept in place.

The size of the new orifice provided by the encapsulation envelope is visualized and measured by radiography or transesophageal echocardiography. Should the orifice area be deemed insufficient, the orifice can be dilated via a balloon-valvuloplasty, as by removing the catheter, and inserting a dilation balloon through the cannula. After any such dilation of the encapsulation envelope to a desired new orifice size, the implement 47 with the valve 55 may again be placed in the aortic orifice to function as a temporary valve.

With the desired size of the new orifice now ascertained, an expandable prosthetic valvular device of appropriate size is chosen. The catheter is removed, and a delivery implement 61 having with the crimped valvular device mounted thereupon is loaded in another catheter, inserted through the cannula and placed at the orifice of the encapsulation envelope under the control of radiography or transesophageal echocardiography. Precise positioning of the delivery implement 61 is achieved by carefully maneuvering its flexible tip. Once in the exact position, as shown in FIG. 23, the sets of strings 63a and 63b restraining the proximal and distal rings 33, 31 of the heart valve stent are released, allowing the stent to expand. Position and orientation of the valvular device are controlled by radiography or transesophageal echocardiography with the delivery implement 61 still in place. If the position of the valvular device is not completely satisfactory, the stent 29 can be reduced in diameter by tightening the two sets of strings so as to allow the valvular device to be repositioned or even completely removed.

Once the final placement desired has been obtained, the delivery implement 61 is removed, while leaving the strings 63 in place. Valve function and effective orifice area are then observed by radiography or transesophageal echocardiography. If the orifice of the implanted valve is deemed to be too small, having the strings 63 in place facilitates another dilation being performed; the valve can be dilated using the dilation balloon method earlier mentioned. Guided by the strings 63b attached to the basal ring portion 33 of the stent 29, the dilation balloon is placed at the basal ring and inflated to expand the nested rings. Once the final diameter of the valve is satisfactory, the string loops are each cut at one arm and pulled out via the other arm.

When a surgeon decides to employ a combined stent/envelope device 67 of the type shown in FIGS. 7 and 8, instead of using a separate encapsulation envelope and a separate valvular device as described just above, the initial portion of the implantation procedure remains the same as described above. Basically, employment of a combined valve/envelope prosthesis, such as one having the encapsulation envelope framework/valve stent 67, allows a single unit to be directly implanted after the primary aortal-valvuloplasty has been accomplished and the appropriate size prosthesis has been chosen.

For such an alternative procedure, a delivery implant with a heart valve which incorporates the combined framework/stent mounted thereupon, that is restrained by four sets of looped strings, is loaded in a catheter and inserted through the cannula; it is moved to the desired location in the aortic valve orifice, under control using radiography or transesophageal echocardiography. Precise positioning of the delivery implement is achieved by maneuvering its flexible tip. Once in the exact position, a first set of strings restraining the distal arms 75 is released allowing this distal section of the envelope portion to fold over the leaflets; the implement is then withdrawn proximally (as generally depicted in FIG. 16), to precisely position the prosthesis before releasing the strings which control the distal and proximal rings of the heart valve stent portion, allowing the stent to expand. The strings that restrain the proximal arms 77 are finally released, allowing them to swing outward and effectively sandwich the native valve leaflets. When positioning is completed, the function of the valve is observed by radiography or transesophageal echocardiography. If the position of the valve is not completely satisfactory, the prosthesis can be released and then reduced in diameter by sequentially tightening the various sets of strings, and the valve can be repositioned or even completely removed. Once such repositioning of the valve is deemed satisfactory, the set of strings at the distal arms 75 are released to allow the arms to fold outward and over the free end portions of the leaflets as described before. The previously described steps of the delivery are then repeated. This overall procedure can again be undone by tightening the strings so long as they are in place.

Once final placement is achieved, both sets of strings looped through the tabs 79 at the ends of the distal and proximal arms are cut and removed, and the delivery implement is removed, leaving the strings connected to the two ring portions of the stent in place. Valve function and effective orifice area is observed by radiography or transesophageal echocardiography. If the desired final diameter of the implanted valve has not been achieved, the valve can be dilated using a dilation balloon. Guided by the strings attached to the stent rings, a dilation balloon is placed at the basal ring section 73 and inflated to dilate the stent of the valve and increase the size of the valve orifice. Once placement, positioning and sizing are ascertained to be accurate, one arm of every remaining string is cut, and each string is pulled out via the other arm.

Once it has been finally ascertained that the positioning and functioning of either of these implanted valves are satisfactory by observing valve function, leaflet mobility, transvalvular gradient and regurgitation using transesophageal echocardiography, the procedure is terminated. The delivery device is removed, and the apex of the heart is securely closed by tying the purse-string sutures. The thorax is closed, leaving a thorax drain. If deemed necessary or desirable, heparin effects are reversed by giving an adequate neutralizing dose of Protamin. Anesthesia is stopped and the patient is weaned from the respirator and extubated in the operation room. The patient is then transferred to an Intermediate Care Unit. After a few hours postoperatively, it should be satisfactory to remove the thorax drain. After about 24 hours, the patient may be discharged.

Although the invention has been described with regard to certain preferred embodiments which constitute the best mode known to the inventors for carrying out this invention, it should be understood that various changes and modifications as would be obvious to one of ordinary skill in the art may be made without deviating from the scope of the invention which is set forth in the claims appended hereto. For example, although it was generally indicated that loops of string emanating from spaced apart longitudinal locations along a delivery implement are employed to control movement of a crimped, shape-memory alloy device, it should be understood that various looped string arrangements may be employed. For example, as illustrated in FIG. 25, three separate loops 81, each of which would extend radially outward from an aperture in the delivery implement 47 pass through an eyelet 23 in the ring of the envelope framework, and then return through the next adjacent eyelet 23 and back through the aperture in the implement, thus creating what is referred to as a 120° loop, such as the loops 49*b* in FIGS. 13-18. Alternatively, as depicted in FIG. 26, three loops 83 may be used which each pass first through an eyelet 23 in the central ring, for example, and then are routed 360° around the entire ring to return through the same eyelet; such is referred to as a 360° overlap loop arrangement. Clearly it can be seen that other patterns of looping can alternately be employed; likewise loops of this type may similarly be used to each control one or more of the distal arms, as well as the proximal arms.

Although a preferred anchoring envelope framework 11 is illustrated in FIGS. 1-4, alternative constructions could be employed. For example, as depicted in FIG. 27, a wire mesh form of framework 87 for an encapsulation envelope might be employed; such may be completely formed from a single continuous strand or a plurality of strands of interleaved wire of shape-memory alloy, e.g. Nitinol, or the like. Such could be crimped at a low temperature where it would be superelastic to take a tubular deployment shape, as shown in FIG. 27; however, its "memory" shape (illustrated in FIG. 28) would be such as to have a central convex ring section from which distal and proximal flanking sections extend that would sandwich native valve leaflets therebetween in the folded "memory" orientation. Accordingly, once located in place within the orifice of a malfunctioning aortic valve or the like, the distal section would again fold over the free ends of the leaflets, and the proximal section would swing outward to sandwich the native leaflets therebetween, leaving a central, convex ring section that could interengage with the stent of a separate valvular device, in a manner similar to the nesting of the basal ring 33 of the stent 29 as described hereinbefore. As an alternative to the anchoring device 11 that has distal and proximal arms formed with circular tabs at their ends, an anchoring device 111, as shown in fragmentary perspective in FIG. 35, might be used. This anchoring envelope framework 111 includes a central ring 113 similar to that previously described; however, arms are provided by pairs of parallel bars which are joined at their ends by a U-shaped loop. These parallel bars of the distal arms 117 and the proximal arms 119 are respectively interconnected by a plurality of spacers similar to rungs in a ladder. Advantages of using this alternative construction for the framework 111 include greater surface area contact between the arms 117 and 119 and the respective surfaces of the valve leaflets, and the option of routing the string loops through the arms at a different location than at the very end of the arms, i.e. through the eyelets 21.

Particular features of the invention are emphasized in the claims that follow.

The invention claimed is:

1. An anchoring device for securing a percutaneously implantable replacement heart valve in an existing valve in the human heart, which device comprises:

a framework of generally tubular shape which is constructed of shape-memory material and includes a central portion, a distal portion and a proximal portion that are integral with one another, said distal portion comprising a plurality of individually controllable distal linear arms which are each connected at only one end to said central portion and have a free opposite end, which distal linear arms evert as a result of temperature change and wrap around the free ends of native leaflets of a stenotic or malfunctioning valve to contact downstream surfaces of the valve leaflets, said proximal portion of said framework comprising a plurality of individually controllable, proximally extending proximal linear arms which are each connected at only one end to said central portion and have a free opposite end, which proximal linear arms are constructed to swing radially outward at their free ends toward said everted distal arms and contact upstream-facing surfaces of the native leaflets and secure said framework within the human heart valve, and said distal and proximal linear arms having means at each said opposite end which allows attachment of cords to individually control and retract each of said linear arms.

2. The anchoring device according to claim 1 wherein the shape-memory of said central portion of said framework causes it to radially expand while said proximal arms swing outward to contact upstream surfaces of the native leaflets and sandwich the native valve leaflets between them and said everted distal arms so as to provide a secure anchor for a replacement valvular device to be mounted interior thereof.

3. The anchoring device according to claim 2 wherein said central portion is formed with a surface with a shape that is complementary to and that will securely interengage with a portion of a stent for a replacement valvular device having a complementary shape.

4. The anchoring device according to claim 3 wherein said central portion comprises a ring section having a generally annular surface of inwardly convex shape which accommodates string loop means used to control its radial expansion and to collapse said ring section if desired.

5. The anchoring device according to claim 4 wherein an exterior covering of biocompatible sheet material surrounds said framework, and said central portion has the general shape of a section of a torus.

6. The anchoring device according to claim 1 in combination with a hollow delivery implement, wherein the device is disposed about the exterior surface of said hollow implement through which a plurality of cords are routed that individually control the distally-extending and proximally extending linear arms and that also control the expansion of the anchoring device as its shape-memory alloy material tends to revert to its desired "memory" shape upon warming to body temperature, and wherein a temporary valve element is carried within said hollow delivery implement which valve element can be deployed once said anchoring device is in place so as to serve as a temporary functioning valve.

7. The combination of a hollow delivery implement and an anchoring device, which combination comprises:

a collapsible-expandable anchoring device having a framework of generally tubular shape which is constructed of shape-memory material and includes a central portion, a distal portion and a proximal portion that are integral with one another, said distal portion comprising a plurality of individually controllable distal linear arms which are each connected at only one end to said central portion and have a free opposite end with an opening through which a cord can be passed, which distal linear arms evert as a result of temperature change and wrap around the free ends of native leaflets of a stenotic or malfunctioning valve to contact downstream surfaces of the valve leaflets, and said proximal portion of said framework comprising a plurality of individually controllable, proximal linear arms which are each connected at only one end to said central portion and have a free opposite end with an opening through which a cord can be passed, said proximal linear arms being constructed to swing radially outward at their free ends toward said everted distal arms and contact upstream-facing surfaces of the native leaflets and secure said framework within the human heart valve, a hollow delivery implement for passage through a cannula inserted in the chest of a patient about the exterior surface of which the anchoring device is disposed, and a plurality of cords are routed through said hollow implement individually control the distal and proximal arms by passage through said openings at the end of each said linear arm and also control the expansion of the anchoring device as its shape-memory alloy material tends to revert to its desired "memory" shape upon warming to body temperature.

8. The combination of claim 7 wherein said central portion comprises a ring section having, when expanded, a generally annular surface of inwardly convex shape which is proportioned to securely interengage with a portion of a stent for a replacement valvular device having a complementary shape.

9. The combination of claim 7, wherein said hollow delivery implement has a plurality of holes in the sidewall thereof through which said cords pass that control said proximal arms.

10. The combination of claim 7 wherein a temporary valve element is carried within said hollow delivery implement, which valve element is designed to be deployed from an open end of said hollow delivery implement once said anchoring device is in place so as to serve as a temporary functioning valve.

11. A collapsed anchoring device for securing a percutaneously implantable replacement heart valve within the confines of an existing valve in the human heart that has become stenotic or malfunctioning following its insertion into the body via a catheter, which device comprises:

a framework of generally tubular shape which is constructed of shape-memory material and includes a central portion, a distal portion and a proximal portion that are integral with one another, said distal portion comprising a plurality of individually controllable distal linear arms which are each connected at only one end to said central portion and which have openings at opposite free ends thereof through which cords can be passed, which distal linear arms evert as a result of temperature change and individually wrap around the free ends of native leaflets of a stenotic or malfunctioning valve to contact downstream surfaces of the valve leaflets, and said central portion being expandable radially outward within the orifice of the native valve as a result of its shape memory, and said proximal portion of said framework comprising a plurality of individually controllable, proximal linear arms which are each connected at only one end to said central portion and which have openings at opposite free ends through which cords can be passed, said proximal linear arms being constructed to swing radially outward at their free ends toward said everted distal linear arms and contact upstream-facing surfaces of the native leaflets and secure said framework within the human heart valve, whereby said distal and proximal linear arms are individually controllable via cords that are passed through said openings at said respective free ends thereof.

12. The device according to claim 11 wherein said framework comprises at least three of said distal linear arms and at least three of said proximal linear arms made of shape-memory material, which at least six linear arms have circular eyelets at the free ends thereof to provide said openings through which cords are passed to facilitate individual control of each arm.

13. The device according to claim 11 wherein said central portion of said framework is formed with a C-shaped outwardly concave axial cross section and has openings through which additional cords can be routed to both control such shape-memory expansion of said framework and to effect reduction of the diameter thereof.

14. The device according to claim 13 wherein said central portion comprises a ring section having a generally annular surface of inwardly convex shape which is proportioned to securely interengage with a portion of a stent for a replacement valvular device having a complementary outwardly concave peripheral shape.

* * * * *